United States Patent [19]

Achterrath-Tuckerman et al.

[11] Patent Number: 5,068,233

[45] Date of Patent: Nov. 26, 1991

[54] SYNERGISTIC COMBINATION OF AZELASTINE AND THEOPHYLLINE OR AZELASTINE AND α-MIMETICS

[75] Inventors: Ute Achterrath-Tuckerman, Maintal; Rudolf Aurich, Karben; Jürgen Engel, Alzenau; Helmut Hettche, Dietzenbach; Axel Kleeman, Mühlheim/M, all of Fed. Rep. of Germany

[73] Assignee: Asta Pharma Aktiengesellschaft, Frankfurt, Fed. Rep. of Germany

[21] Appl. No.: 449,318

[22] Filed: Dec. 11, 1989

Related U.S. Application Data

[63] Continuation of Ser. No. 144,176, Jan. 15, 1988, abandoned.

[30] Foreign Application Priority Data

Jan. 17, 1987 [DE] Fed. Rep. of Germany ....... 3701287

[51] Int. Cl.$^5$ .............................................. A61K 31/55

[52] U.S. Cl. .................................... 514/212; 514/264; 514/653; 514/826

[58] Field of Search ................ 514/264, 212, 653, 826

[56] References Cited

PUBLICATIONS

Chem. Abst., 104:122784v (1986).
Chem. Abst., 103:171802n (1985).
Chem. Abst., 103:115902a (1985).
Chem. Abst., 100:96328v (1984).
Chem. Abst., 100:203384i (1984).
Arzneim-Forsch./Drug Res. 31(II) No. 8, pp. 1184–1193, (1981).
Chemical Abstracts 89:123259m (1978).
Chemical Abstracts 95:144027y (1981).

*Primary Examiner*—Leonard Schenkman
*Attorney, Agent, or Firm*—Cushman, Darby & Cushman

[57] ABSTRACT

A medicine having a synergistic activity containing a combination of azelastine and theophylline or azelastine and at least one β-mimetic.

9 Claims, No Drawings

SYNERGISTIC COMBINATION OF AZELASTINE AND THEOPHYLLINE OR AZELASTINE AND α-MIMETICS

This is a continuation of application Ser. No. 07/144,176, filed Jan. 15, 1988, which was abandoned upon the filing hereof.

The present invention relates to a synergistic combination of azelastine with another compound selected from the group consisting of theophylline or a β-mimetic.

BACKGROUND OF THE INVENTION

Azelastine is an anti-asthmatic medicinal agent having antiallergic and antihistaminic properties. Its chemical name is 4-(p-chlorobenzyl)-2-[N-methyl-perhydroazepinyl)(4)]-1-(2H)-phthalazinone. It has the following structural formula:

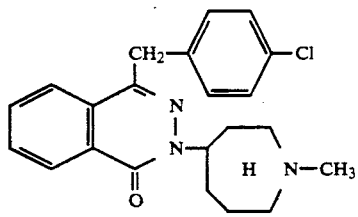

Azelastine and its salts with physiologically acceptable acids are effective primarily because of antihistaminic and antiallergic activity, but they also have a slight bronochospasmolytic effect.

β-mimetics are medicinal agent with pronounced bronochospasmolytic activity. Examples of these compounds are: reproterol (7-{3[(β,3,5-trihydroxyphenethyl)-amino]propyl}-theophylline), salbutamol, terbutaline fenoterol, procaterol, clenbuterol and orciprenaline.

SUMMARY OF THE INVENTION

The object of the present invention is to provide improved medicaments with asthma prophylactic, antiallergic and antihistaminic activity for human medicine and for veterinary medicine.

In accordance with the present invention, it has been found that the activity of azelastine and its salts is enhanced by combination with a member of the group consisting of theophylline and β-mimetics and their salts. In addition, the bronchospasmolytic activity of the theophylline or the bronchospasmolytic activity of the β-mimetic also displays a simultaneous synergistic increase. The active substances of the combination of the invention thus have a mutually potentiating effect.

More specifically, the present invention provides novel medicinal compositions as well as a method of treating patients with those compositions. The compositions contain as active substances either synergistically effective amounts of azelastine and theophylline or synergistically effective amounts of azelastine and at least one β-mimetic or salts of these compounds with physiologically acceptable acids also in individually separate formulations. Preferably the composition contains one part by weight of azelastine for each case 0.2 to 10,000 parts by weight of theophylline or for each one part by weight of azelastine, 0.0001 to 1000 parts by weight of β-mimetic. The amounts by weight or parts by weight relate in each case to the pure active substances, in other words not to components included to convert the active substances to salts. Should salts be used, the amounts change according to the modified gram-molecular weight of the salts.

The azelastine and the β-mimetics are preferably used as acid addition salts, with particular preference being given to salts with hydrohalo acids (for example hydrochlorides, hydrobromides) and also to salts with organic acids (for example embonic acid, maleic acid, citric acid, tartaric acid). Theophylline is generally not used in the form of the salt. Should it be used as a salt, it is for example a salt with choline (2-hydroxy-N,N,N-trimethylethane). It is, however, also possible to use theophylline in the form of a complex (for example with 2-amino-2-methyl propanol 1:1 or ethanolamine 1:1 or magnesium acetate 1:1 or N-methyl glucamine 1:1) or as a mixture or compound with ethylene diamine as described in the Europaeische Arzneibuch, Volume II, page 370-371 or DAB 9, page 1377-1378.

In the spasmolysis test, for example, the combination of the invention displays a synergistic effect on the antihistaminic activity which is enhanced to a super additive extent as compared to the antihistaminic activity of the pure azelastine and the pure theophylline or the β-mimetic.

The combination of the invention has a surprising functional synergism. The activity of the combination of the invention is demonstrated for example in the following experiments. These trials were conducted in association with the histamine spasm test in isolated guinea pig ileum. Here, for example, the azelastine dosage (hydrochloride) is maintained constant and the dosage of theophylline or β-mimetic (for example reproterol) is changed and in each case intestinal spasm inhibition is determined as a % of uninhibited histamine spasm (Method of determining synergism according to Magnus).

Description of the experiment (isolated guinea pig ileum):

Guinea pigs of both sexes having a mean weight of 400-600 g are stunned by a blow on the neck and exsanguinated. The lower part of the small intestine above the bottom 10 cm before the transition to the large intestine is dissected, flushed with cold Tyrode's solution and incubated in a refrigerator for 1 hour. 3-4 cm long sections are then cut and suspended in the immersion baths (Tyrode's solution[1]) 37° C., carbogen gassing[2]) under isotonic conditions, a tension of 2 g being applied. Following an adjustment time of 30 minutes the contraction in response to a standard spasmogen concentration of histamine ($2 \times 10^{-7}$ mol/liter) is determined. After a constant standard spasm has been obtained (+/−10% of mean value) the spasmolytic activity of the experimental concentrations is determined singly for both the same organ and its activity determined. The effects of the individual components and their combination are compared with one another.

1 Tyrode's solution: standardized, glucose-containing nutrient solution that has the same osmotic pressure as blood
2 Carbogen: gaseous mixture of 95% oxygen and 5% carbon dioxide.

The results are set out in tables 1 and 2.

TABLE 1

| | % inhibition (histamine $2 \times 10^{-10}$ mol/ml | |
|---|---|---|
| Azelastine.HCl (μg/ml) | | |
| 0.001 * | 38.9 ± 19.9 | N = 8 |

TABLE 1-continued

| | % inhibition (histamine $2 \times 10^{-10}$ mol/ml) | |
|---|---|---|
| 0.001 ** | 49.3 ± 1.9 | N = 4 |
| 0.001 *** | 9.4 ± 12.4 | N = 8 |
| 0.001 **** | 46.3 ± 34.6 | N = 8 |
| Theophylline (μg/ml) | | |
| 10 * | 9.0 ± 12.8 | N = 8 |
| 20 ** | 25.0 ± 15.1 | N = 4 |
| 40 *** | 39.6 ± 26.9 | N = 8 |
| 60 **** | 20.6 ± 15.5 | N = 8 |
| Azelastine.HCl (0.001 μg/ml) + Theophylline (μg/ml) | | |
| 10 * | 52.6 ± 23.2 | N = 8 |
| 20 ** | 54.8 ± 7.5 | N = 4 |
| 40 *** | 66.4 ± 12.4 | N = 8 |
| 60 **** | 73.1 ± 18.0 | N = 8 |

* always designate groups that belong together
N = number of animals used in each case

TABLE 2

| | % inhibition (histamine $2 \times 10^{-10}$ mol/ml) | |
|---|---|---|
| Azelastine.HCl (μg/ml) | | |
| 0.001 * | 35.1 ± 25.7 | N = 8 |
| 0.001 ** | 26.6 ± 15.1 | N = 8 |
| 0.001 *** | 45.9 ± 21.1 | N = 8 |
| Reproterol.HCl (μg/ml) | | |
| 0.02 * | 14.5 ± 16.6 | N = 8 |
| 0.04 ** | 14.5 ± 18.1 | N = 8 |
| 0.06 *** | 48.5 ± 21.3 | N = 8 |
| Azelastine.HCl + Reproterol.HCl (μg/ml) 0.001 + | | |
| 0.02 * | 64.4 ± 16.9 | N = 8 |
| 0.04 ** | 54.3 ± 13.1 | N = 8 |
| 0.06 *** | 74.3 ± 24.1 | N = 8 |

* always designate the groups that belong together
N = number of animals used in each case Thus for example in the above described test the antihistaminic activity of azelastine is increased by 26% (mean value) from 36% (mean value).

The antihistaminic activity of theophylline is for example increased from 24% (mean value) by 38% (mean value) upon addition of azelastine.

The antihistaminic activity of reproterol is increased from 26% (mean value) by 38% (mean value) on addition of azelastine.

The daily dosages of the combination of the invention are for example 0.1 to 30 mg, preferably 0.5 to 20 mg and in particular 1 to 10 mg of azelastine and 50 to 1000 mg, preferably 80 to 600 mg, in particular 100 to 500 mg of theophylline or 0.1 to 30 mg, preferably 0.5 to 20 mg and in particular, 1 to 10 mg azelastine and 0.01 to 200 mg, preferably 0.02 to 100 mg, in particular 0.05 to 50 mg of β-mimetic.

The daily dosages may be given in the form of a single administration of the total amount or in the form of 1 to 10, in particular 1 to 5 partial dosage per day. In general a dosage of 1 to 4 times, in particular 1 to 3 times daily is preferred. For example, the preferred dosage for the combination of azelastine and theophylline is 0.5 to 10 mg of azelastine and about 100 to 300 mg of theophylline or 0.1 to 10 mg of azelastine and 0.01 to 20 mg of reproterol, 1 to 4 times daily. In particular this dosage is about 4 mg of azelastine and about 250 mg of theophylline or 4 mg of azelastine and 10 mg of reproterol 1 to 3 times daily.

In accordance with the invention azelastine and theophylline are used for example in the following weight ratios: 1 part by weight of azelastine is for example used or combined with 0.3 to 10,000 parts by weight of theophylline, preferably 1 part by weight of azelastine with 4 to 3000 parts by weight of theophylline, in particular 1 part by weight of azelastine with 20 to 1000 parts by weight of theophylline.

In accordance with the invention azelastine and the β-mimetic (or a mixture of different β-mimetics) are for example used in the following weight ratios: 1 part by weight of azelastine is, for example, applied or combined with 0.0001 to 1000, preferably 0.001 to 250, in particular 0.005 to 40 parts by weight of β-mimimetic. In the case of reproterol for example, 1 part by weight of azelastine is applied or combined with 0.0003 to 500 parts by weight, preferably 0.005 to 100 parts by weight, in particular with 0.05 to 50 parts by weight of reproterol.

For example for the combination, 10 to 500 mg of theophylline and 0.05 to 30 mg of azelastine, preferably 100 to 400 mg of theophylline and 0.2 to 15 mg of azelastine, in particular 100 to 300 mg of theophylline and 0.5 to 10 mg of azelastine may easily be formulated into a medicament.

For example for the combination 0.005 to 200 mg of a β-mimimetic (such as for example 0.005–50 mg of reproterol) and 0.1 to 30 mg of azelastine, preferably 0.01 to 150 mg of β-mimetic (such as for example 0.03 to 30 mg of reproterol) and 0.3 to 20 mg of azelastine, in particular 0.03 to 100 mg of β-mimetic (such as for example 0.1 to 20 mg of reproterol) and 0.5 to 10 mg of azelastine may easily be formulated into a medicament.

The amounts by weight given hereinabove apply in particular to homogeneous mixtures of theophylline and azelastine or of β-mimetic and azelastine (for example suppositories or single-layer tablets). For other formulations, for example capsules and double-layer tablets, the components may of course also be combined together in other amounts by weight.

The dosage unit of the combination of the invention may for example contain:

(a) For oral medicinal forms:

0.1 to 30 mg of azelastine, preferably 0.5 to 20 mg, in particular 1 to 10 mg of azelastine and 0.005 to 100 mg, preferably 0.01 to 50 mg, in particular 0.05 to 30 mg of β-mimetic, such as for example 1 to 50 mg, preferably 5 to 40 mg, in particular 10 to 20 mg of reproterol.

In the case of fenoterol and terbutaline the following amounts may for example be used: 0.1 to 20, preferably 0.5 to 10, in particular 1 to 7 mg (amount of azelastine as given above).

In the case of salbutamol the following amounts may for example be used: 0.01 to 10, preferably 0.05 to 1, in particular 0.1 to 0.8 mg; in the case of sustained release preparations (and also suppositories) for example 0.1 to 15, preferably 0.5 to 10 mg (amount of azelastine as given above).

In the case of clenbuterol the following amounts may for example be used: 0.005 to 1, preferably 0.01 to 0.1, in particular 0.01 to 0.05 mg (amount of azelastine as given above). These dosages may for example be administered 1 to 5, preferably 1 to 4, in particular 1 to 3 times daily.

(b) In the case of parenteral medicinal forms (for example intravenous, intramuscular; per 1 ml):

0.05 to 30 mg of azelastine, preferably 0.1 to 20 mg, in particular 0.2 to 10 mg or also 0.3 to 5 mg of azelastine and 0.01 to 5 mg, preferably 0.03 to 1 mg, in particular 0.05 to 0.5 mg of β-mimetic such as for example 0.01 to 1 mg, preferably 0.03 to 0.5 mg, in particular 0.05 to 0.1 mg of reproterol. In the case of fenoterol and terbutaline the following amounts may for example be used: 0.01 to 5, preferably 0.1 to 1, in particular 0.2 to 0.7 mg (amount of azelastine as given above).

These dosages may for example be administered 1 to 5, preferably 1 to 4, in particular 1 to 3 times daily.

c) In the case of medicinal forms for application on the skin and mucous membranes (for example as solutions, lotions, emulsions, ointments, plasters and so on):

5 to 50 mg of azelastine, preferably 5 to 30 mg, in particular 10 to 20 mg of azelastine and 10 to 200 mg, preferably 25 to 100 mg, in particular 40 to 80 mg of β-mimimetic, such as for example 10 to 100 mg, preferably 25 to 75 mg, in particular 30 to 60 mg of reproterol.

These dosages may for example be administered 1 to 5, preferably 1 to 4, in particular 1 to 2 times daily.

d) In the case of medicinal forms for inhalation (for example in the form of aerosols or dusting powders; per aerosol actuation):

0.1 to 10 mg of azelastine, preferably 0.1 to 5 mg, in particular 0.1 to 3 mg of azelastine and 0.005 to 100 mg, preferably 0.008 to 8 mg, in particular 0.01 to 5 mg of β-mimetic such as for example 0.05 to 5 mg, preferably 0.10 to 3 mg, in particular 0.3 to 2 mg of reproterol.

In the case of fenoterol and terbutaline the following amounts may for example be used: 0.02 to 2 mg, preferably 0.05 to 1 mg, in particular 0.1 to 0.5 mg (amount of azelastine as given above).

In the case of salbutamol the following amounts may, for example, be used: 0.01 to 1, preferably 0.02 to 0.5 mg, in particular 0.05 to 0.3 mg (amount of azelastine as given above).

These dosages may for example be administered 1 to 10, preferably 1 to 5, in particular 1 to 3 times daily.

When used in conjunction with theophylline, the dosage unit of the combination of the invention may for example contain:

a) In the case of peroral medicinal forms or medicinal forms for rectal or vaginal application:

0.1 to 30 mg of azelastine, preferably 0.5 to 20 mg, in particular 1 to 10 mg of azelastine and 100 to 500 mg, preferably 100 to 400 mg, in particular 100 to 300 mg of theophylline.

These dosages may for example be administered 1 to 5, preferably 1 to 4, in particular 1 to 3 times daily.

b) In the case of parenteral medicinal forms (for example intravenous, intramuscular):

0.05 to 30 mg of azelastine, preferably 0.1 to 20 mg, in particular 0.3 to 10 mg of azelastine and 10 to 500 mg, preferably 30 to 400 mg, in particular 50 to 300 mg of theophylline.

These dosages may for example be administered 1 to 5, preferably 1 to 4, in particular 1 to 3 times daily.

c) In the case of medicinal forms for application to the skin and mucous membranes (for example as solutions, lotions, emulsions, ointments, plasters and so on):

5 to 50 mg of azelastine, preferably 5 to 30 mg, in particular 10 to 20 mg of azelastine and 100 to 1000 mg, preferably 250 to 750 mg, in particular 250 to 700 mg of theophylline.

These dosages may for example be administered 1 to 5, preferably 1 to 4, in particular 1 to 3 times daily.

It is of course also possible to manufacture pharmaceutical formulations which contain the given dosage units 2 to, for example, 200 times. In particular tablets or capsules of the combination contain 0.2 to 500 mg, pellets, powders and granulates containing 0.5 to 100 mg, metered aerosols contain 0.5 to 1000 mg of the azelastine component.

The dosages and parts by weight quoted hereinabove, which relate to application in man, are in each case related to the free bases or free acids.

The acute toxicity of the combination of the invention in the mouse (expressed as $LD^{50}$ mg/kg; method: Litchfield and Wilcoxon, J. Pharmacol. Exper. Ther. 95:99, 1949) for the combination of azelastine and theophylline (4:100) for oral application is for example in the order of 350 mg/kg, or above 300 mg/kg body weight.

The acute toxicity of the combination of the invention in mice (expressed as $LD^{50}$ mg/kg; method: Litchfield and Wilcoxon, J. Pharmacol. Exper. Ther. 95:99, 1949) for the combination of azelastine and reproterol (1:5) for oral application is for example in the order of 1700 mg/kg, or more than 1000 mg/kg body weight.

The pharmaceutical compositions or medicaments contain as active substance the combination of the invention in a formulation. The individual active ingredients of the combination may, however, also be present in separate formulations in each case, with the already mentioned amounts of active substance being used in each case for the appropriate dosage unit. The active substances or the combination of active substances is optionally present in a mixture with other pharmacologically or pharmaceutically active substances. The manufacture of the medicament is effected in known manner, whereby the known and customary pharmaceutical auxiliary substances as well as other conventional carrier and diluting agents may be used.

Carrier and auxiliary substances which may for example be used are those substances which are recommended or listed in the following literature references as being auxiliary substances for pharmaceutical, cosmetic and related fields: Ullmann's Encyklopaedie der technischen Chemie, Volume 4 (1953), page 1 to 39; Journal of Pharmaceutical Sciences, Volume 52 (1963), page 918 et. seq., H.v.Czetsch-Lindenwald, Hilfsstoffe füer Pharmazie und angrenzende Gebiete; Pharm. Ind., Issue 2, 1961, page 72 et seq.; Dr. H. P. Fiedler, Lexikon der Hilfsstoffe fuer Pharmazie, Kosmetik und angrenzende Gebiete, Cantor KG, Aulendorf/Wuerttemberg, 1981.

Suitable examples are gelatin, natural sugar such as sucrose or lactose, lecithin, pectin, starch (for example corn starch), cyclodextrin and cyclodextrin derivatives, polyvinyl pyrrolidone, polyvinylacetate, gelatin, gum arabic, alginic acid, tylose, talc, lycopodium, silica gel (for example colloidal), cellulose, cellulose derivatives (for example cellulose ether in which the cellulose hydroxy groups have been partially etherified with lower saturated aliphatic alcohols and/or lower saturated aliphatic oxyalcohols, for example methyloxypropyl cellulose, methyl cellulose, hydroxypropylmethyl cellulose, hydroxypropylmethyl cellulose phthalate); fatty acids as well as magnesium, calcium or aluminum salts of fatty acids with 12 to 22 carbon atoms, in particular of the saturated (for example stearates) emulsifiers, oils and fats, in particular vegetable oils, (for example peanut oil, castor oil, olive oil, sesame oil, cotton seed oil, corn oil, wheat germ oil, sunflower seed oil, cod liver oil, also hydrated in each case; mono-, di- and triglycerides of saturated fatty acids $C_{12}H_{24}O_2$ to $C_{18}H_{36}O_2$ and their mixtures), pharmaceutically acceptable mono or polyvalent alcohols and polyglycols such as polyethylene glycols as well as derivatives thereof, esters of aliphatic saturated or unsaturated fatty acids (2 to 22 carbon atoms, in particular 10 to 18 carbon atoms) with monovalent aliphatic alcohols (1 to 20 carbon atoms) or multivalent alcohols such as glycols, glycerol, diethylene glycol, pentaerythritol, sorbitol, mannitol and so on, which may optionally also be etherified, esters of citric acid with primary alcohols and acetic acid, benzylbenzoate, dioxolane, glycerol formal, tetrahydrofurfuryl alcohol, polyglycol ethers with $C_1$–$C_{12}$ alcohols, dimethylacetamide, lactamide, lactates, ethylcarbonate, silicones (in particular medium viscous polydimethylsiloxanes), calcium carbonate, sodium carbonate, calcium phosphate, sodium phosphate, magnesium carbonate and the like. Other auxiliary substances that may be used include substances that effect disintegration (so-called disintegrating agents) such as: cross-linked polyvinyl pyrrolidone, sodium carboxymethyl starch, sodium carboxymethyl cellulose or microcrystalline cellulose. Conventional coating substances may also be used. These may for example be: polymerizates as well as copolymerizates of acrylic acid and/or methacrylic acid and/or their esters; hydroxypropylmethyl cellulose phthalate- or -acetate succinate; cellulose-, starch- and polyvinylacetate phthalate; carboxymethyl cellulose; methylcellulose phthalate-, -succinate, -phthalate succinate as well as phthalic acid half-ester; zein; ethyl cellulose and -succinate; shellac; gluten; ethylcarboxyethyl cellulose; ethacrylate-maleic acid anhydride copolymer; maleic acid anhydride vinylmethylether copolymer; styrol maleic acid copolymerizate; 2-ethylhexylacrylate maleic acid anhydride; crotonic acid vinylacetate copolymer; glutamic acid/glutamic acid ester copolymer; carboxymethylethyl cellulose glycerine monooctanoate; cellulose acetate succinate; polyarginine.

Plasticizing agents that may be used for coating substances include: citric and tartaric acid esters (acetyltriethyl-, acetyltributyl-, tributyl-, triethylcitrate); glycerol and glycerol esters (glycerol diacetate, -triacetate, acetylated monoglycerides, caster oil); phthalic acid ester (dibutyl-, diamyl-, diethyl-, dimethyl-, dipropyl-), D-(2-methoxy- or ethoxyethyl-)phthalate, ethylphthalyl-, butylphthalylethyl- and butylglycolate; alcohols (propylene glycol, polyethylene glycols of different chain lengths), adipates (diethyl-, di(2-methoxy- or ethoxyethyl adipate); benzophenone; diethyl- and dibutylsebacate, -succinate, -tartrate; diethyleneglycol dipropionate; ethyleneglycol diacetate, -dibutyrate, -dipropionate; tributylphosphate, tributyrin; polyethyleneglycol sorbitan monooleate; sorbitan monooleate.

For the production of solutions it is for example possible to use water or physiologically acceptable organic solvents such as ethanol, 1,2-propylene glycol, polyglycols and their derivatives, dimethylsulfoxide, fatty alcohols, triglycerides, partial esters of glycerol, paraffins and the like. For injectable solutions or suspensions it is for example possible to use non-toxic parenterally acceptable diluting agents or solvents, such as: water, 1,3-butanediol, ethanol, 1,2-propylene glycol, polyglycols mixed with water, Ringer's solution, isotonic sodium chloride solution, or also solidified oils including synthetic mono- or diglycerides or fatty acids such as oleic acid.

In the preparation of the formulations it is possible to use known and conventional dissolving agents or emulsifiers. Dissolving agents and emulsifiers that may for example be used include: polyvinyl pyrrolidone, sorbitan fatty acid esters such as sorbitan trioleate; phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolated oleotriglycerides, polyethyleneoxide condensation products of fatty alcohols, alkylphenols or fatty acids or also 1-methyl-3-(2-hydroxyethyl)-imidazolidone-(2). In this context, polyoxyethylated means that the relevant substances contain polyoxyethylene chains, the degree of polymerization of which generally lies between 2 and 40 and, in particular, between 10 and 20.

Such polyoxyethylated substances may, for example, be obtained through reaction of hydroxyl group containing compounds (for example mono or diglycerides or unsaturated compounds such as for example those containing oleic acid radicals) with ethylene oxide (for example 40 mol of ethylene oxide per mol glyceride).

Examples of oleotriglycerides are olive oil, peanut oil, castor oil, sesame oil, cotton seed oil, corn oil. See also Dr. H. P. Fiedler "Lexikon der Hilfsstoffe für Pharmazie, Kosmetik und angrenzende Gebiete" 1971, p. 191–195.

It is, moreover, also possible to add preservatives, stabilizers and buffers, for example calcium hydrogen phosphate, colloidal aluminum hydroxide, taste correcting agents, sweeteners, clorants, antioxidants and complexing agents (for example ethylenediaminetetraacetic acid) and the like. The active substance molecule may optionally be stabilized through adjustment with physiologically acceptable acids or buffers to a pH range of between ca. 3 to 7. In general a neutral or weakly acid (up to pH 5) pH value is preferred.

Propellants that may for example be used for metered aerosol inhalers are: fluorinated chlorinated hydrocarbons such as trichlorofluoromethane, dichlorodifluoroethane, trichlorotrifluoroethane, symmetrical dichlorotetrafluoroethane, dimethylether, propane, butane, carbon dioxide.

Antioxidants that may be used are, for example, sodium metabisulphite, ascorbic acid, gallic acid, alkyl gallates, butylhydroxyanisole, nordihydroguaiaretic acid, tocopherols as well as tocopherols+synergistic agents (substances which bind heavy metals through complex formation, for example lecithin, ascorbic acid, phosphoric acid). The addition of synergistic agents considerably enhances the antioxidizing activity of the tocopherols.

Preservatives that may be used are for example sorbic acid, p-hydroxybenzoic acid esters (for example lower alkyl esters), benzoic acid, sodium benzoate, trichloroisobutyl alcohol, phenol, cresol, benzethonium chloride and formalin derivatives.

The pharmaceutical treatment and formulation of the active substances is carried out using conventional standard methods. For example active substance(s) and auxiliary or carrier substances are well mixed by means of stirring or homogenization (for example using conventional mixers), generally working at temperatures between 20° and 80° C., preferably 20° to 50° C., in particular at room temperature. Reference is made furthermore to the following standard reference work: Sucker, Fuchs, Speiser, Pharmazeutische Technologie, Thieme-Verlag, Stuttgart, 1978.

Application may be to the skin or mucous membrane or to the inside of the body, for example oral, enteral, pulmonal, rectal, nasal, vaginal, lingual, intravenous, intra-arterial, intracardial, intramuscular, intraperitoneal, intracutaneous, subcutaneous.

In the case of parenteral formulations these are in particular sterile or sterilized products.

The combination of the invention may also be present in the form of a product in which the two individual active substances are present in separate formulations so that administration may also be separate or at different times.

Should such separate formulations be present, these are adapted to one another and contain the appropriate active substances in the dosage unit in the amounts and corresponding weight ratios in which they may be present in the combined mixture.

When given separately it is also possible for the two partners of the combination not to be administered at the same time. In such cases the $\beta$-mimetic (for example reproterol) may be given 5 to 60 minutes before or 5 to 240 minutes after administration of the azelastine. In the case of the combination of azelastine and theophylline the following applies: Prior administration of theophylline 5 to 60 minutes before azelastine or 5 to 240 minutes after azelastine.

DETAILED DESCRIPTION OF PREFERRED EMBODIMENTS

Example 1

Tablets containing 3 mg of azelastine hydrochloride and 300 mg of theophylline monohydrate or containing 1 mg of azelastine hydrochloride and 100 mg of theophylline monohydrate:

A paste prepared from 18 g of corn starch and 333 g of water is used for granulation of a mixture of 9 g of finely pulverized azelastine hydrochloride and 300 g of microcrystalline cellulose in a conventional manner. After drying, the granulate is passed through a sieve of mesh size 1 mm and then mixed with 900 g of theophylline monohydrate, 180 g of microcrystalline cellulose, 86.1 g of modified starch (Starch 1500/Colorcon), 0.9 g of highly dispersed silicon dioxide and 6 g of magnesium stearate. The finished mixture is pressed into oblong tablets weighing 500 mg, that are 18 mm long and 8 mm wide.

The tablets may then optionally be provided with a film coating in a conventional manner.

Each tablet contains 3 mg of azelastine hydrochloride and 300 mg of theophylline monohydrate.

In a similar manner, tablets containing 1 mg of azelastine hydrochloride and 100 mg of theophylline monohydrate can be prepared by pressing the above mentioned prepared mixture into tablets weighing 166.6 mg that are 8 mm in diameter.

Example 2

Tablets containing 3 mg of azelastine hydrochloride and 20 mg of reproterol hydrochloride or 1.5 mg of azelastine hydrochloride and 10 mg of reproterol hydrochloride:

150 g of azelastine hydrochloride are intensively mixed with 1000 g of reproterol hydrochloride, 4000 g of lactose, 1000 g of corn starch, 1000 g of microcrystalline cellulose and 90 g of highly dispersed silicon dioxide and then granulated with 2.5 kg of 8% corn starch slurry using the conventional process. After drying, the granulate is pressed through a sieve of mesh size 1 mm and mixed with 1500 g of microcrystalline cellulose, 525 g of corn starch, 500 g of talcum, 10 g of highly dispersed silicon dioxide and 25 g of magnesium stearate. The finished mixture is pressed into oblong tablets weighing 200 mg that are 11 mm long and 5.5 mm wide.

The tablets may optionally be provided with a film coating using a conventional process.

Each tablet contains 3 mg of azelastine hydrochloride and 20 mg of reproterol hydrochloride.

In a similar manner it is possible to produce tablets containing 1.5 mg of azelastine hydrochloride and 10 mg of reproterol hydrochloride by preparing the above mentioned finished mixture into tablets weighing 100 mg having a diameter of 6 mm and a radius of curvature of 4 mm.

Example 3

Suppositories containing 3 mg of azelastine hydrochloride and 100 mg of theophylline monohydrate or 1 mg of azelastine hydrochloride and 300 mg of theophylline monohydrate:

15 g of azelastine hydrochloride and 500 g of theophylline monohydrate are suspended in 9.835 kg of melted hard fat[3]. (see Europaeisches Arzneibuch, Volume III). After homogenization, the suspension is poured into hollow molds of 2.3 ml in the conventional manner and allowed to cool.

[3] Hard fat is a mixture of mono-, di- and triglycerides of the saturated fatty acids of $C_{10}H_{20}O_2$ to $C_{18}H_{36}O_2$.

A suppository weighing 2.07 g contains 3 mg of azelastine hydrochloride and 100 mg of theophylline monohydrate.

In analogous manner it is possible to manufacture suppositories containing 1 mg of azelastine hydrochloride and 300 mg of theophylline monohydrate by suspending 5 g of azelastine hydrochloride and 1500 g of theophylline monohydrate in 9245 g of melted hard fat, but proceeding otherwise in a similar manner.

Example 4

Suppositories containing 3 mg of azelastine hydrochloride and 10 mg of reproterol hydrochloride or 1 mg of azelastine hydrochloride and 20 mg of reproterol hydrochloride:

15 g of azelastine hydrochloride and 50 g of reproterol hydrochloride are suspended in 10.135 kg of melted hard fat. Following homogenization, the suspension is poured into hollow molds of 2.3 ml in the conventional manner and allowed to cool.

A suppository weighing 2.04 g contains 3 mg of azelastine hydrochloride and 10 mg of reproterol hydrochloride.

In analogous manner it is possible to prepare suppositories containing 1 mg of azelastine hydrochloride and 20 mg of reproterol hydrochloride by suspending 5 g of azelastine hydrochloride and 100 g of reproterol hydrochloride in 10.095 kg of melted hard fat, the procedure being otherwise as described above.

Example 5

Metered aerosol containing 1.0 mg of azelastine hydrochloride and 0.5 mg of reproterol hydrochloride per stroke:

450 g of dichlorodifluoromethane are cooled down to about $-50°$ C. and 14 g of sorbitan trioleate suspended therein. 20 g of azelastine hydrochloride and 10 g of reproterol hydrochloride are added to the suspension in portions with intensive stirring. The so obtained suspension is made up with dichlorodifluoromethane to 859.6 g. 526.4 g of 1,2-dichlorotetrafluoroethane are then added under stirring and cooling. The suspension is then cooled down to ca. −50° C. with further stirring and filled with continuous stirring in 13.86 g batches into aluminum cans which are subsequently sealed using conventional commercial dosage valves (for example using metal dosage valves supplied by Riker/3M). The dosage valves release 0.05 ml of aerosol suspension per stroke. Each stroke thus delivers 1 mg of azelastine hydrochloride and 0.5 mg of reproterol hydrochloride.

Example 6

Sustained release tablets containing 400 mg of theophylline monohydrate and 5 mg of azelastine hydrochloride 5 g of azelastine hydrochloride are intensively mixed in portions with 200 g of hydroxypropyl cellulose (viscosity of a 2% aqueous solution: 150–400 cps) and 200 g of hydroxypropylcellulose (viscosity of a 2% aqueous solution: 6–10 cps) as well as 400 g of theophylline monohydrate and the mixture is pressed dry in the conventional manner. The product so obtained (comprimate) is ground to a particle size of under 0.4 mm and 5 g of magnesium stearate are then added. The mixture obtained thereby is pressed into oblong tablets weighing 810 mg, that are 19 mm long and 8 mm wide. The tablets may optionally subsequently be provided with a gastric juice soluble film coating in the conventional manner.

Each tablet contains 400 mg of theophylline monohydrate and 5 mg of azelastine hydrochloride in a formulation having sustained release of the active substance.

Example 7

Hard gelatin capsules containing 350 mg of theophylline monohydrate in sustained release form and 5 mg of azelastine hydrochloride 400 g of theophylline monohydrate are mixed with 10 g of microcrystalline cellulose and 7 g of hydroxypropyl cellulose (viscosity of the 5% solution 75–150 cps) and the mixture made into a paste with 60 g of a 6.25% aqueous solution of hydroxypropyl cellulose. The wet mass is pressed through a conventional perforated metal disc with a hole diameter of 1 mm and the resultant filaments are divided and rounded off in the conventional manner using a spheronizer disc. The pellets so obtained are dried and sieved. 400 g of pellets of the sieve fraction 800–1200 μm are coated in the conventional manner with a solution of 42.5 g ethyl cellulose and 37.5 g of polyethylene glycol 1500 in 720 g of chloroform by spraying in a fluidized bed apparatus.

70 g of azelastine hydrochloride are intensively mixed with 400 g of lactose, 97 g of corn starch, 100 g of microcrystalline cellulose and 9 g of highly disperse silicon dioxide and subsequently granulated with 250 g of 8% corn starch slurry in a conventional manner. After drying, the granulate is passed through a sieve of mesh size 1 mm and mixed with 3 g of magnesium stearate add 1 g of highly dispersed silicon dioxide.

50 mg of the mixture so obtained is filled, together with, in each case, 465 mg of the above obtained coated pellets into size 0 hard gelatin capsules.

Each hard gelatin capsule contains 350 mg of theophylline monohydrate in sustained release form and 5 mg of azelastine hydrochloride.

Example 8

Sustained release tablets containing 30 mg of reproterol hydrochloride and 5 mg of azelastine hydrochloride.

600 g of reproterol hydrochloride, 100 g of azelastine hydrochloride, 2200 g of hydroxypropylmethyl cellulose (viscosity of a 2% aqueous solution: 4000 cP), 2600 g of spray-dried lactose and 60 g of magnesium stearate are mixed and the mixture is pressed to round tablets weighing 278 mg, having a diameter of 9 mm and a radius of curvature of 9 mm.

Subsequently the tablets may be provided with a gastric juice resistant film coating using conventional methods.

Each sustained release tablet contains 30 mg of reproterol hydrochloride and 5 mg of azelastine hydrochloride.

Example 9

Formulations using other β-mimetics a) Sustained release tablets containing 7.5 mg of terbutaline sulfate and 5 mg of azelastine hydrochloride 150 g of terbutaline sulfate, 100 g of azelastine hydrochloride, 960 g of hydroxypropylmethyl cellulose[4], 1170 g of spray dried lactose and 20 g of magnesium stearate are mixed and the mixture pressed into round tablets weighing 120 mg, having a diameter of 6 mm and a radius of curvature of 6 mm.

[4] Viscosity of a 2% aqueous solution: 4000cP

Subsequently the tablets may be provided with a gastric juice soluble film coating using conventional methods.

Each sustained release tablet contains 7.5 mg of terbulatine sulphate and 5 mg of azelastine hydrochloride.

b) Sustained release tablets containing 10 mg of salbutamol sulphate and 5 mg of azelastine hydrochloride The method described in a) is repeated with 200 g of salbutamol sulphate instead of 150 g of terbutaline sulphate and 1120 g of spray dried lactose in place of 1170 g of spray dried lactose.

c) Sustained release tablets with 5 mg of fenoterol hydrobromide and 5 mg of azelastine hydrochloride The method described in a) is repeated with 100 g of fenoterol hydrobromide in place of 150 g of terbutaline sulphate and 1220 g of spray dried lactose in place of 1170 g of spray dried lactose.

What is claimed is:

1. A pharmaceutical composition useful for the treatment of asthmatic, antiallergic and antihistaminic symptoms and also with asthma prophylactic activity containing as active substances a member of the group consisting of (a) a synergistic combination of azelastine and theophylline in an amount of 3 to 5000 parts by weight for each part by weight of azelastine, or (b) a synergistic combination of azelastine and at least one β-mimetic or salts of these compounds with physiologically acceptable acids in an amount of 0.0003 to 1000 parts by weight for each part of weight of azelastine.

2. A dosage unit of a pharmaceutical product or composition useful for the treatment of asthmatic, antiallergic and antihistaminic symptoms and also with asthma prophylactic activity as set forth in claim 1, which contains 0.1 to 50 mg of azelastine and either 10 to 1000 mg of theophylline or 0.005 to 200 mg of β-mimetic.

3. A dosage unit as set forth in claim 2 which contains 0.2 to 20 mg of azelastine and 80 to 600 mg of theophylline.

4. A dosage unit as set forth in claim 2 which contains 1 to 10 mg of azelastine and 1 to 50 mg of β-mimetic or 1 to 10 mg of azelastine and 80 to 500 mg of theophylline.

5. A pharmaceutical composition useful for the treatment of asthmatic, antiallergic and antihistaminic symptoms as set forth in claim 1 including a pharmaceutically acceptable carrier.

6. A method of treating a patient exhibiting asthmatic, allergic or other symptoms which are responsive to antihistaminic medications which comprises concurrently, or separately administering to said patient, (a) a synergistic combination of azelastine and theophylline in an amount of 3 to 5000 parts by weight of each part by weight of azelastine, or (b) a synergistic combination of azelastine and at least one β-mimetic or salts of these compounds with physiologically acceptable acids in an amount of 0.0003 to 1000 parts by weight for each part by weight of azelastine.

7. A method as set forth in claim 6 in which the azelastine and the member of the group consisting of theophylline and β-mimetics, or salts of these compounds with physiologically acceptable acids are administered at different times.

8. A method as set forth in claim 7 in which a β-mimetic is administered 5 to 60 minutes before or 5 to 240 minutes after azelastine.

9. A method as set forth in claim 7 in which theophylline is administered 5 to 60 minutes before or 5 to 240 minutes after azelastine.

* * * * *